United States Patent [19]

Kaibel et al.

[11] Patent Number: 4,833,379

[45] Date of Patent: May 23, 1989

[54] MOTOR CONTROL FAIL-SAFE CIRCUIT

[75] Inventors: Gary W. Kaibel, Troy, Mo.; Frederick F. Schweitzer, Watertown, N.Y.

[73] Assignee: Sherwood Medical Company, St. Louis, Mo.

[21] Appl. No.: 144,803

[22] Filed: Jan. 13, 1988

[51] Int. Cl.[4] .............................................. H02P 7/06
[52] U.S. Cl. ..................................... 388/811; 307/246; 307/594; 361/89; 388/810; 388/918; 388/921
[58] Field of Search ................................ 318/339–341; 361/89, 94, 103–104; 307/239–246, 590, 592–594, 600, 605

[56] References Cited

U.S. PATENT DOCUMENTS

| | | | |
|---|---|---|---|
| 3,215,896 | 11/1965 | Shattuck et al. | 361/104 |
| 3,348,099 | 10/1967 | Schweitzer et al. | 361/104 |
| 3,466,527 | 9/1969 | Chun | 361/104 |
| 3,700,968 | 12/1971 | Spies | 361/104 |
| 3,719,858 | 8/1971 | Gilbreath | 361/104 |
| 4,258,404 | 3/1981 | Challet | 361/104 |
| 4,280,161 | 7/1981 | Kuhn et al. | 361/104 |

Primary Examiner—William M. Shoop, Jr.
Assistant Examiner—David Martin
Attorney, Agent, or Firm—Darby & Darby

[57] ABSTRACT

A fail-safe circuit is disclosed for use with an intermittently operated d.c. motor connected by means of a circuit breaker to a power supply, wherein a control circuit provides control pulses intermittently to the motor. The fail-safe circuit includes a capacitor which is charged when the drive pulses are being applied to said motor, and is discharged when the drive pulses are not being applied to said motor. A reference voltage is generated and compared with the voltage stored on said capacitor. When the voltage on the capacitor exceeds the reference voltage, the circuit breaker is caused to interrupt the power supply to the motor.

5 Claims, 1 Drawing Sheet

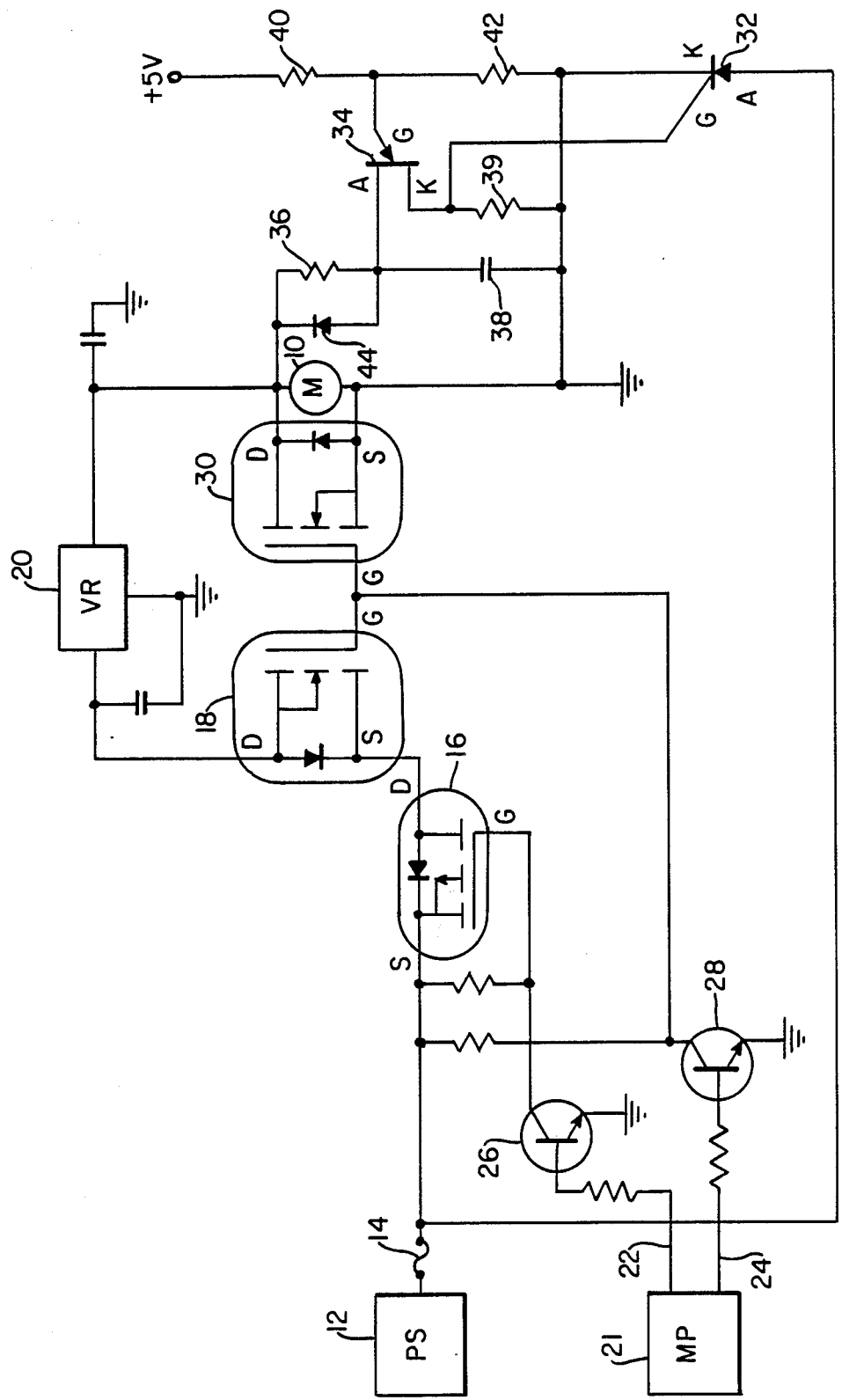

MOTOR CONTROL FAIL-SAFE CIRCUIT

This invention relates to a fail-safe circuit for a d.c. motor. More specifically, this invention relates to a fail-safe circuit which interrupts the power supply to an intermittently operated d.c. motor if the motor is caused to run continuously.

Infusion pumps used for the delivery of nutrients and other fluids to patients typically operate on an intermittent or periodic basis. For example, an enteral feeding pump sold by Sherwood Medical Company under the trademark KANGAROO comprises a motor driven peristaltic pump which supplies nutrients to a patient on a periodic basis. The device is microprocessor controlled so that a predetermined dose can be fed to the patient. Normally, the pump operates periodically (for example, one rotation of the pump rotor every ten seconds) until the desired dosage has been supplied.

If the control circuitry for the motor which operates the pump fails, there is a chance that the motor will remain on. In the case of an enteral feeding pump, such a failure will cause the patient to be overfed with potentially fatal consequences. Similarly, the possibility of overdosing in a drug infusion system can be life threatening.

Accordingly, the principal object of this invention is to provide a fail-safe circuit for use with an intermittently operated d.c. motor which will cause the motor to be turned off if, because of a failure in the control circuitry, the motor operates continuously for more than a preselected time period.

SUMMARY OF THE INVENTION

A fail-safe circuit in accordance with the invention is intended to be used with a d.c. motor connected to a power supply by means of a conventional circuit breaker such as a fuse. A control circuit provides intermittent drive pulses for the motor. The fail-safe circuit includes a capacitor which is charged by the drive pulses at the same time the pulses are applied to the motor. The capacitor discharges when the drive pulses are not being supplied to the motor. A reference voltage of preselected magnitude is established and means are provided for comparing the reference voltage to the voltage stored on the capacitor. If, due to a failure of the control circuit, the motor is caused to operate continuously for more than a predetermined time, the voltage on the capacitor will exceed the reference voltage. Should this happen, the comparison means causes the circuit breaker to interrupt the power supply to the motor.

THE DRAWING

The drawing is a circuit diagram showing a preferred embodiment of the invention for use with a d.c. motor intended to drive a peristaltic enteral feeding pump.

DETAILED DESCRIPTION

Referring to the drawing, the motor is shown at 10. In a preferred embodiment, motor 10 drives a peristaltic enteral feeding pump. The power for motor 10 is provided by a standard d.c. power supply 12 over a line which includes a circuit breaker 14, for example, a 0.5 amp fuse. The direct current is fed through normally non-conducting MOSFET's 16 and 18 and voltage regulator 20 which may apply regulated five volt pulses to motor 10.

In the preferred embodiment, motor 10 is controlled by a microprocessor 21 which provides for the capability of dose control among other things. The precise control of the motor forms no part of this invention, for which purposes it is only necessary to know that microprocessor 21 produces a "power on" signal on line 22 and motor drive pulses on line 24. The "power on" signal on line 22 causes transistor 26 to conduct which, in turn, grounds the gate G of MOSFET 16 causing the MOSFET 16 to conduct so that the direct voltage from the power supply 12 is applied to the source electrode of MOSFET 18.

When microprocessor 21 provides a pulse on line 24, transistor 28 conducts which grounds the gate G of MOSFET 18 causing it to conduct so that the d.c. source is applied to voltage regulator 20 and motor 10. Hence, the motor starts to operate.

A MOSFET 30 is connected in parallel with MOSFET 18 in the motor control circuit. MOSFET 30 is the complement of MOSFET 18, i.e., it closes (conducts) when MOSFET 18 is open (not conducting) and vice versa. Hence, when the motor is not operating, MOSFET 18 is not conducting and MOSFET 30 is conducting. When the drive pulses on line 24 cause MOSFET 18 to conduct, MOSFET 30 simultaneously is rendered non-conducting so that motor 10 can operate. The purpose of MOSFET 30 is to provide a positive stop for motor 10 when the drive pulse on line 24 terminates. Thus, when MOSFET 18 becomes non-conducting, the conduction of MOSFET 30 shorts the leads of the motor causing prompt termination of motor rotation.

In normal operation, the pulses on line 24 operate the motor 10 on a periodic basis, for example causing a single revolution of the peristaltic enteral feeding pump (not shown) so that the patient receives the desired dose. If, because of a malfunction, the motor 10 operates continuously an overdose is caused. The invention provides a fail-safe circuit which breaks the motor drive circuit by means of fuse 14 if the motor 10 remains on for a preselected period of time, for example ten seconds, which in practice may represent three complete revolutions of the rotor of the peristaltic pump.

The fail-safe circuit, in accordance with the invention, comprises a silicon controlled rectifier (SCR) 32 and a unijunction transistor 34 in conjunction with an RC circuit consisting of a resistor 36 and capacitor 38. SCR 32 is connected to the d.c. power supply 12 in parallel with motor 10 and functions as a normally closed gating means in series with fuse 14. A resistor 39 provides a voltage for the gate of SCR 32 and prevents false triggering of the SCR.

Resistors 40 and 42 are connected between ground and a five volt source to provide a reference voltage at the gate G of the unijunction transistor 34. This reference voltage maintains the unijunction transistor 34 normally non-conducting. When a pulse from the voltage regulator 20 causes motor 10 to operate, current also flows through resistor 36 to the capacitor 38, causing the capacitor to charge. Normally, when the motor drive pulses on line 24 cease, capacitor 38 will discharge through diode 44 and MOSFET 30 which is closed (conducting) in the absence of the drive pulses. If, for any reason, the motor 10 continues to operate, the MOSFET 30 remains open (non-conducting) and, therefore capacitor 38 cannot discharge, in which case the voltage at the junction of resistors 36 and capacitor 38 increases.

For the unijunction transistor 34 to conduct, the voltage on the anode A must exceed the voltage on the gate G. As indicated, the gate voltage is established by the reference voltage at the junction of resistors 40 and 42. When capacitor 38 charges to a voltage which exceeds this reference voltage the unijunction transistor 34 conducts which, in turn, applies a positive voltage to the gate G of SCR 32. This causes the SCR 32 to conduct and, since its cathode K is connected to ground, an extremely high current is drawn from the power supply 12 which blows the fuse 14. This removes the power supply from the motor which therefore cannot run regardless of any failures in the control circuit. By selecting the values of resistor 36 and capacitor 38, one can control the time required to charge the capacitor to the reference level (i.e., the maximum allowable time during which the motor can operate continuously).

What is claimed is:

1. For use with an intermittently operated d.c. motor connected by means of a circuit breaker to a power supply and including a control circuit comprising two switching means one of which is conducting when the other is non-conducting, one of said switching means transferring drive pulses intermittently to said motor, the other shorting the motor when said drive pulses are removed, a fail-safe circuit comprising:
   a normally open switching means in series with said circuit breaker means,
   a capacitor,
   means for charging said capacitor when said drive pulses are being applied to said motor,
   means for discharging said capacitor when said drive pulses are not being applied to said motor,
   means for generating a reference voltage,
   means for comparing the reference voltage with the voltage stored on said capacitor, and
   means for closing said normally open switching means when the voltage on said capacitor exceeds said reference voltage to cause said circuit breaker to interrupt the power supply circuit to said motor.

2. A fail-safe circuit according to claim 1, wherein said means for discharging said capacitor includes the switching means which shorts the motor when the drive pulses are removed.

3. A fail-safe circuit according to claim 2, wherein said means for comparing comprises a unijunction transistor and said normally open switching means comprises a silicon controlled rectifier connected to said unijunction transistor.

4. In combination, a d.c. power supply, a d.c. motor, circuit breaker means connecting said motor to said power supply, a control circuit comprising two switching means one of which is conducting when the other is non-conducting, one of said switching means transferring drive pulses intermittently to said motor, the other shorting the motor when said drive pulses are removed, and a fail-safe circuit, comprising:
   a normally open switching means in series with said circuit breaker means,
   a capacitor,
   means for charging said capacitor when said drive pulses are being applied to said motor,
   means for discharging said capacitor when said drive pulses are not being applied to said motor,
   means for generating a reference voltage,
   means for comparing the reference voltage with the voltage stored on said capacitor, and
   means for closing said normally open switching means when the voltage on said capacitor exceeds said reference voltage to cause said circuit breaker means to interrupt the power supply circuit to said motor.

5. The combination according to claim 4, wherein said means for discharging said capacitor includes the switching means which shorts the motor when the drive pulses are removed.

* * * * *